(12) United States Patent
Sommers

(10) Patent No.: US 8,092,505 B2
(45) Date of Patent: Jan. 10, 2012

(54) BONE NAIL

(75) Inventor: Mark B. Sommers, Beaverton, OR (US)

(73) Assignee: Acumed LLC, Hillsboro, OR (US)

( * ) Notice: Subject to any disclaimer, the term of this patent is extended or adjusted under 35 U.S.C. 154(b) by 436 days.

(21) Appl. No.: 12/361,447

(22) Filed: Jan. 28, 2009

(65) Prior Publication Data

US 2009/0192512 A1 Jul. 30, 2009

Related U.S. Application Data

(60) Provisional application No. 61/062,769, filed on Jan. 28, 2008.

(51) Int. Cl.
*A61B 17/84* (2006.01)
*A61B 17/86* (2006.01)

(52) U.S. Cl. ......................... 606/329; 606/317

(58) Field of Classification Search ............... 606/62, 606/64, 67, 104, 300, 301, 312, 315, 317, 606/329; 411/394

See application file for complete search history.

(56) References Cited

U.S. PATENT DOCUMENTS

| | | | | |
|---|---|---|---|---|
| 327,296 | A | * | 9/1885 | McGinnis ..................... 411/454 |
| 1,951,278 | A | * | 3/1934 | Axel ............................... 606/67 |
| 2,419,555 | A | | 4/1947 | Fator |
| 3,351,054 | A | * | 11/1967 | Florek ............................ 606/62 |
| 3,466,748 | A | | 9/1969 | Christensen |
| 3,977,142 | A | | 8/1976 | Dove et al. |
| 4,175,555 | A | | 11/1979 | Herbert |
| 4,463,753 | A | | 8/1984 | Gustilo |
| 4,479,783 | A | | 10/1984 | Weissman |
| 4,723,541 | A | | 2/1988 | Reese |
| 4,746,294 | A | | 5/1988 | Colombo et al. |
| 4,978,349 | A | | 12/1990 | Frigg |
| 4,978,350 | A | | 12/1990 | Wagenknecht |
| 5,145,373 | A | | 9/1992 | Roane |
| 5,211,647 | A | * | 5/1993 | Schmieding ................... 606/104 |
| 5,217,462 | A | | 6/1993 | Asnis et al. |
| 5,226,766 | A | | 7/1993 | Lasner |
| 5,259,398 | A | * | 11/1993 | Vrespa .......................... 128/898 |
| 5,269,686 | A | | 12/1993 | James |

(Continued)

FOREIGN PATENT DOCUMENTS

FR 2681777 4/1993

(Continued)

OTHER PUBLICATIONS

Jones, Emily, Examiner, U.K. Intellectual Property Office, U.K. Patent Application Serial No. GB0901385.5, Patents Act 1977: Combined Search and Examination Report Under Sections 17 and 18(3); search date: May 19, 2009; examination report date: May 20, 2009.

*Primary Examiner* — Thomas C. Barrett
*Assistant Examiner* — Christian Sevilla
(74) *Attorney, Agent, or Firm* — Kolisch Hartwell, PC

(57) ABSTRACT

System, includes devices, methods, and kits, for fixing bone and/or repairing connective tissue associated with bone using a fastener constructed as a bone nail that includes at least one helical ridge having a large pitch. The large pitch permits the nail to be driven into bone by application of axial force to the nail, to secure the nail in the bone. In some embodiments, the bone nail may have a variable pitch that decreases toward the trailing end of the nail.

18 Claims, 7 Drawing Sheets

U.S. PATENT DOCUMENTS

| | | | |
|---|---|---|---|
| 5,300,074 A | | 4/1994 | Frigg |
| 5,375,957 A | * | 12/1994 | Golledge ..................... 411/453 |
| 5,403,136 A | | 4/1995 | Mathys |
| 5,472,444 A | | 12/1995 | Huebner et al. |
| 5,562,672 A | | 10/1996 | Huebner et al. |
| 5,693,055 A | | 12/1997 | Zahiri et al. |
| 5,697,930 A | | 12/1997 | Itoman et al. |
| 5,709,687 A | | 1/1998 | Pennig |
| 5,730,744 A | * | 3/1998 | Justin et al. .................... 606/304 |
| 5,741,256 A | | 4/1998 | Bresina |
| 5,766,174 A | | 6/1998 | Perry |
| 5,871,486 A | | 2/1999 | Huebner et al. |
| 5,908,422 A | | 6/1999 | Bresina |
| 5,964,768 A | | 10/1999 | Huebner |
| 5,993,477 A | | 11/1999 | Vaitekunas et al. |
| 6,030,162 A | | 2/2000 | Huebner |
| 6,059,785 A | | 5/2000 | Schavan et al. |
| 6,187,007 B1 | * | 2/2001 | Frigg et al. ..................... 606/293 |
| 6,197,031 B1 | | 3/2001 | Barrette et al. |
| 6,261,292 B1 | | 7/2001 | Diebold et al. |
| 6,299,615 B1 | | 10/2001 | Huebner |
| 6,319,253 B1 | * | 11/2001 | Ackeret et al. ................. 606/64 |
| 6,379,360 B1 | * | 4/2002 | Ackeret et al. ................. 606/67 |
| 6,409,730 B1 | | 6/2002 | Green et al. |
| 6,663,634 B2 | | 12/2003 | Ahrens et al. |
| 6,811,552 B2 | | 11/2004 | Weil, Sr. et al. |
| 6,984,235 B2 | | 1/2006 | Huebner |
| 7,070,601 B2 | | 7/2006 | Culbert et al. |
| 7,182,765 B2 | * | 2/2007 | Roth et al. ....................... 606/62 |
| 7,306,600 B2 | | 12/2007 | Roth et al. |
| 2004/0106925 A1 | | 6/2004 | Culbert |
| 2005/0101961 A1 | | 5/2005 | Huebner et al. |
| 2005/0273107 A1 | | 12/2005 | Stevens |
| 2006/0149247 A1 | * | 7/2006 | Frigg et al. ...................... 606/64 |
| 2006/0271054 A1 | | 11/2006 | Sucec et al. |
| 2007/0142837 A1 | | 6/2007 | Dreyfuss |
| 2007/0260248 A1 | | 11/2007 | Tipirneni |
| 2008/0177291 A1 | | 7/2008 | Jensen et al. |

FOREIGN PATENT DOCUMENTS

| | | |
|---|---|---|
| JP | 06-42515 A | 2/1994 |
| JP | 08-284942 A | 11/1996 |
| JP | 09-144734 A | 6/1997 |
| JP | 10-213110 A | 8/1998 |
| WO | 9322983 | 11/1993 |
| WO | 9420040 | 9/1994 |

* cited by examiner

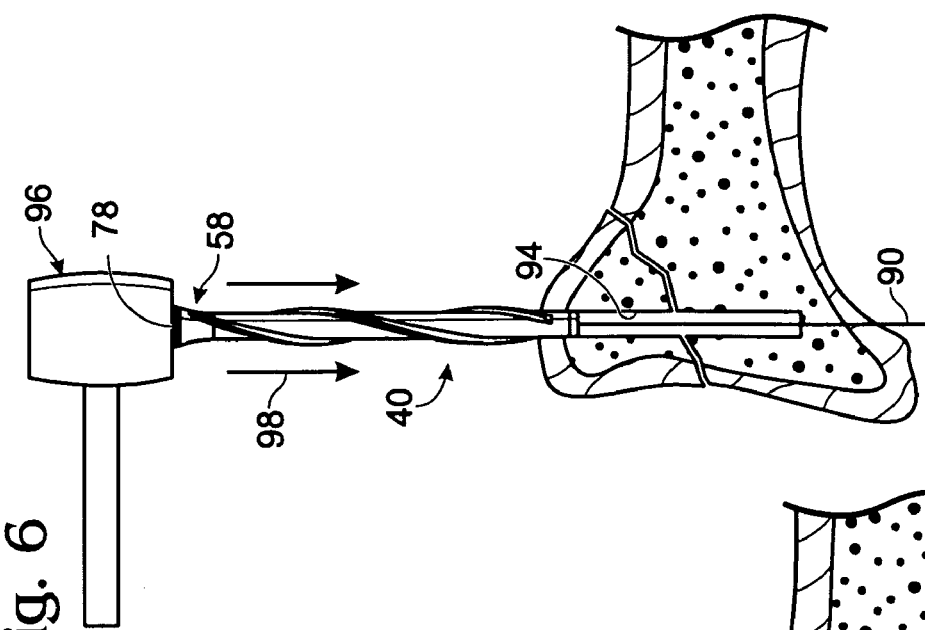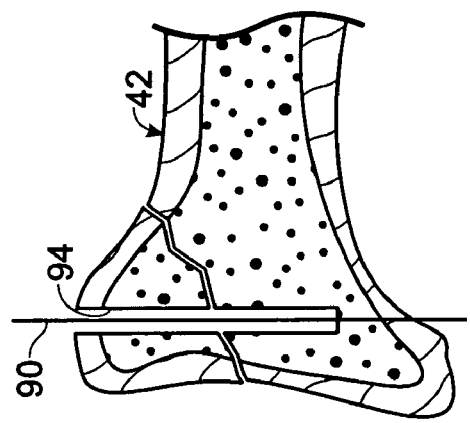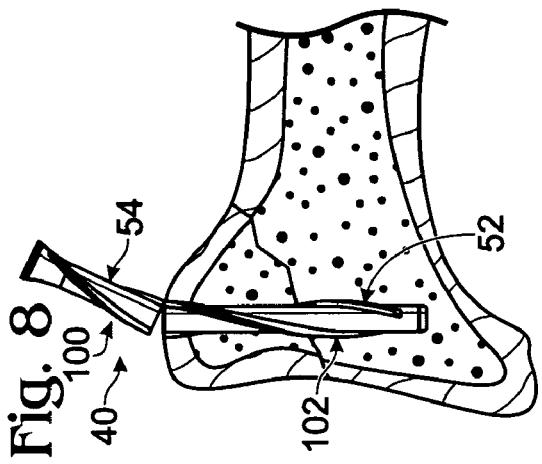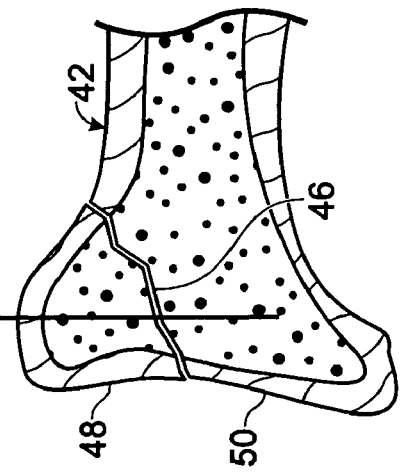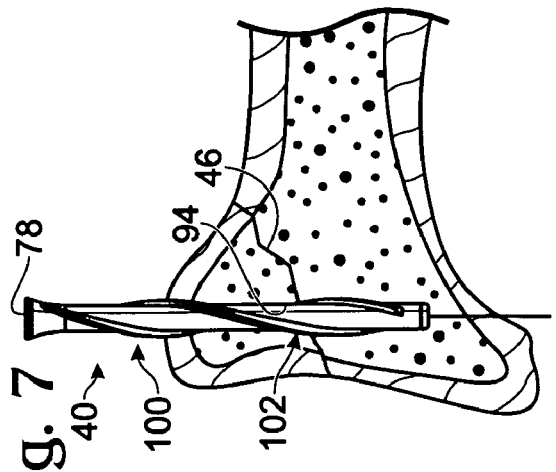

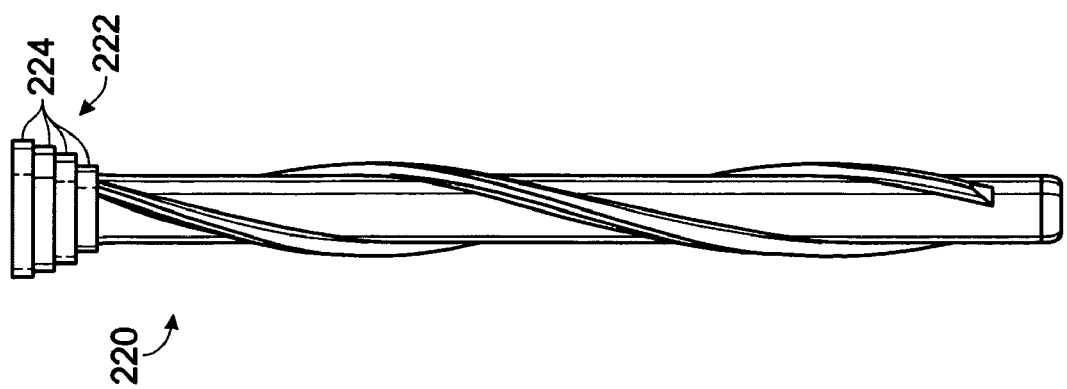
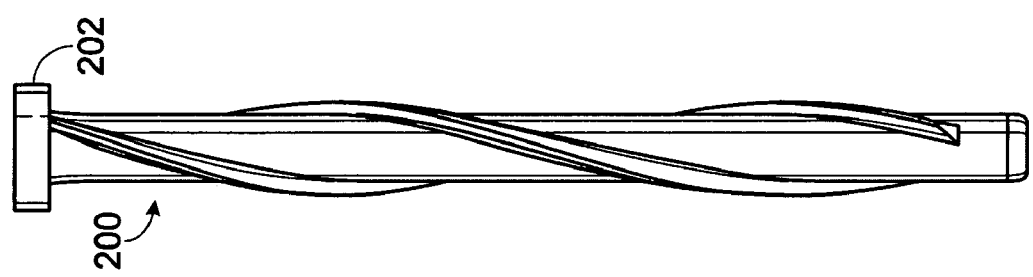
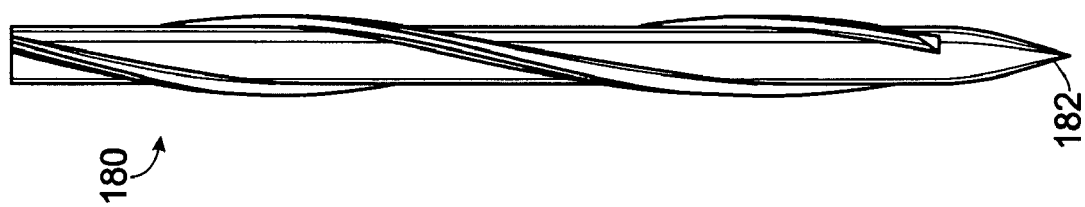
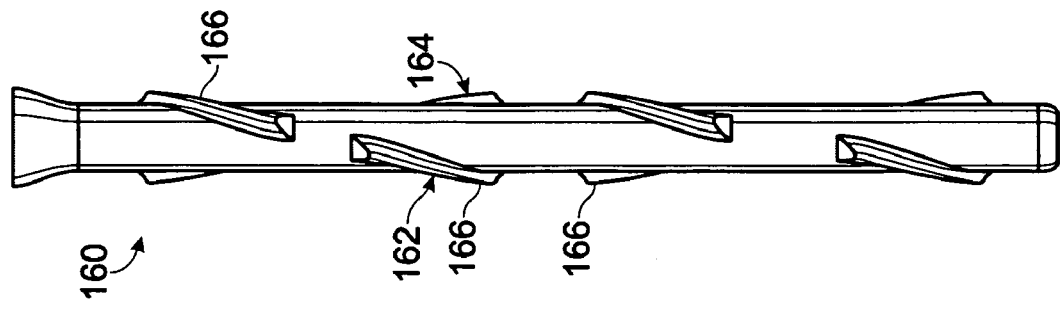

BONE NAIL

CROSS-REFERENCE TO PRIORITY APPLICATION

This application is based upon and claims the benefit under 35 U.S.C. §119(e) of U.S. Provisional Patent Application Ser. No. 61/062,769, filed Jan. 28, 2008, which is incorporated herein by reference in its entirety for all purposes.

INTRODUCTION

The human skeleton is composed of 206 individual bones that perform a variety of important functions, including support, movement, protection, storage of minerals, and formation of blood cells. To ensure that the skeleton retains its ability to perform these functions, and to reduce pain and disfigurement, bones that become fractured should be repaired promptly and properly. Typically, fractured bones are treated using fixation devices, which reinforce the fractured bones and keep them aligned during healing. Fixation devices may take a variety of forms, including casts for external fixation, and bone screws or pins for internal fixation, among others.

Bone screws and pins are rod-shaped fasteners that may be installed in bone to hold fragments of fractured bones in place to fix the bones. These two types of fasteners differ fundamentally, however, in the manner in which they are installed.

A bone screw includes an external thread and a structure for engagement with a rotationally operated driver (e.g., a screwdriver). The bone screw is advanced into bone by turning the bone screw with the driver, which transmits torque to the bone screw. Bone screws may be used alone or in combination with an orthopedic implant (e.g., a bone plate or intramedullary nail) to fasten the orthopedic implant to bone.

A bone pin, in contrast, may be designed to be advanced into bone by applying an axial force to a trailing end of the pin. Accordingly, the bone pin may be driven into a pre-drilled hole in bone by striking the bone pin one or more times with an impact tool, such as a hammer or mallet. The hole may be undersized such that the pin fits tightly in the bone. The entire bone pin may be implanted into bone or an external, trailing portion of the pin may be cut from the pin after a suitable leading portion of the pin has been placed into bone.

Bone pins may have advantages over bone screws. For example, bone pins may be easier to install, generally providing more flexibility in selecting a depth of placement and overall fastener length, and do not strip threads in bone during placement. Furthermore, bone pins are often smaller in diameter than bone screws and therefore may damage bone less and may provide greater flexibility in selecting the site of implantation.

However, bone pins may be inferior to bone screws for many orthopedic applications. For example, bone pins may be more likely to slip axially and/or rotationally. As a result, bone pins may be unsuitable in many cases for holding bone fragments aligned and providing compression between the bone fragments. However, both factors generally are required for anatomic restoration and proper bone healing. Thus, there is a need for an improved bone pin.

SUMMARY

The present disclosure provides a system, includes devices, methods, and kits, for fixing bone and/or repairing connective tissue associated with bone using a fastener constructed as a bone nail that includes at least one helical ridge having a large pitch. The large pitch permits the nail to be driven into bone by application of axial force to the nail, to secure the nail in the bone. In some embodiments, the bone nail may have a variable pitch that decreases toward the trailing end of the nail.

BRIEF DESCRIPTION OF THE DRAWINGS

FIGS. 4-8 are a series of sectional views of the fractured bone of FIG. 1 in configurations produced during performance of an exemplary method of bone fixation using the nail of FIGS. 1-3, in accordance with aspects of the present disclosure.

FIG. 14 is a side view of a fourth exemplary embodiment of a bone nail constructed in accordance with aspects of present disclosure, with the bone nail including helical ridges that are discontinuous, thereby forming ridge segments.

FIG. 15 is a side view of a fifth exemplary embodiment of a bone nail constructed in accordance with aspects of the present disclosure, with the bone nail having a pointed tip and being solid instead of hollow.

FIG. 16 is a side view of a sixth exemplary embodiment of a bone nail constructed in accordance with aspects of present disclosure, with the bone nail including a head that projects orthogonally to the long axis of the bone plate.

FIG. 17 is a side view of a seventh exemplary embodiment of a bone nail constructed in accordance with aspects of the present disclosure, with the bone nail including a stepped head.

DETAILED DESCRIPTION

Figure 1:
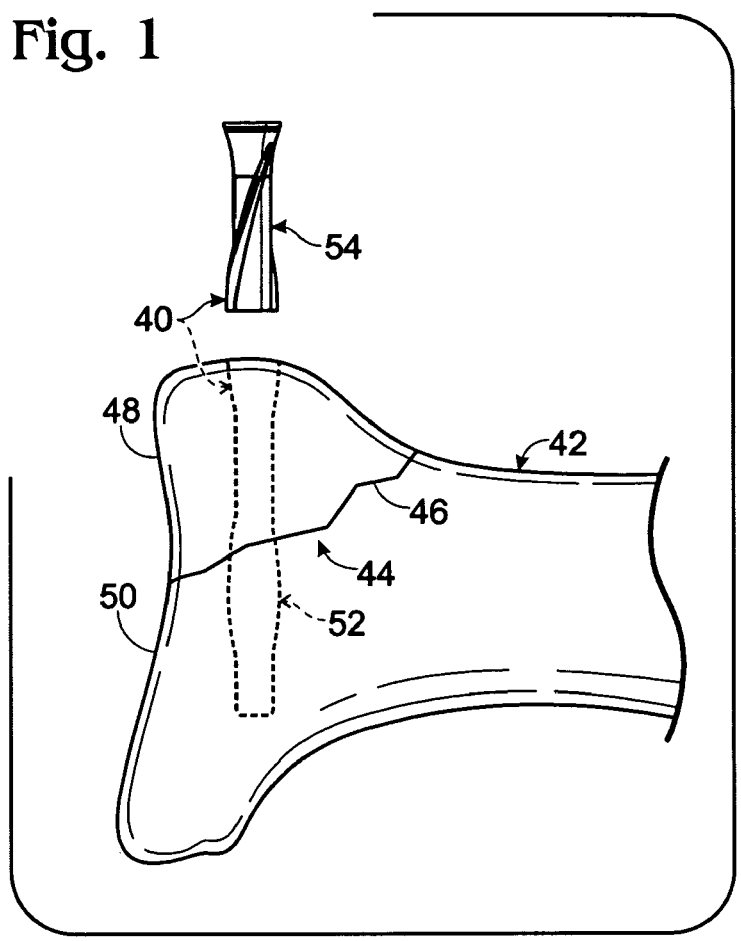
FIG. 1 is a view of a first exemplary embodiment of a bone nail including helical ridges of large pitch, with a leading piece of the bone nail fixing a fractured bone after separation of the bone nail into two discrete pieces, in accordance with aspects of the present disclosure.

The present disclosure provides a system, includes devices, methods, and kits, for fixing bone and/or repairing connective tissue associated with bone using a fastener constructed as a bone nail that includes at least one helical ridge having a large pitch. The large pitch permits the nail to be driven into bone by application of axial force to the nail, to secure the nail in the bone. In some embodiments, the bone nail may have a variable pitch that decreases toward the trailing end of the nail.

A device for bone fixation may comprise a nail including a shaft, which may be slender and/or substantially cylindrical. The nail optionally may include a head extending from the shaft. For example, the nail may be flared near a trailing end thereof to form the head. Accordingly, the head may be wider than and tapered toward the shaft. The nail and the shaft each may have a respective length. The shaft may define a central and/or long axis and may extend along at least most or all of the length of the nail. The nail also may include one or more helical ridges formed on the shaft along at least most of the length of the nail and at least substantially centered on the central axis. The helical ridges may or may not be formed on only a minor portion of a circumference of the shaft. Each helical ridge may have a large pitch, namely, an average lead angle of greater than fifty degrees, such as an average lead angle of about sixty to eighty degrees. In some embodiments, each helical ridge may have a lead angle of at least about fifty degrees along at least most of the helical ridge. In any event, each helical ridge extends more axially than circumferentially on the shaft such that the nail is capable of being driven into threaded relation with bone by application of one or more pulses of axial force to the nail.

The nail may include or lack any suitable features. In some embodiments, the nail may be dividable conceptually into a leading portion and a trailing portion arranged axially along the nail. The pitch of each helical ridge may be variable, for example, the pitch may be greater in the leading portion than in the trailing portion and may decrease gradually and/or smoothly towards the trailing end of the nail, thereby providing compression of the bone when the nail is driven into the bone. In some embodiments, the leading portion and the trailing portion may be leading and trailing halves of the nail, as determined by length. In some embodiments, the shaft and/or at least one helical ridge may taper toward a leading end of the nail, optionally along at least most of the length of the shaft and/or of the at least one helical ridge. If the at least one helical ridge is tapered, the helical ridge may taper in width, in height, or both. In some embodiments, each helical ridge may project at least generally radially from the shaft to an average and/or maximum height that is less than an average radius of the shaft, and/or the average width of each helical ridge may be less than an average width of a helical surface of the shaft formed between an adjacent pair of the helical ridges. In some embodiments, the shaft and the helical ridges may collectively form a body of the nail with the shaft forming most of the body's volume. In some embodiments, the helical ridges may be formed along at least most of the length of both the leading half and the trailing half of the nail.

A method of bone fixation may comprise selecting a nail as disclosed herein and driving the nail into bone. The nail, optionally including at least a portion of a head thereof, may be driven at least partially into a bone to place the nail across a discontinuity in the bone by application of one or more pulses of axial force to the nail such that the helical ridges cause the nail to turn and form grooves in the bone complementary to the helical ridges as the nail is advanced into the bone. As a result of driving, at least part of the nail may be secured in the bone to stabilize pieces of the bone opposingly flanking the discontinuity. In some embodiments, the pitch of the helical ridges may be variable and may decrease toward the trailing end of the nail, thereby providing compression between pieces of the bone that opposingly flank the discontinuity when the nail is driven into the bone.

A method of attaching a band of connective tissue to a bone may comprise selecting a nail and driving the nail into the bone. The nail may include a body portion defining a central axis. The nail also may include two or more helical ridges formed on the body portion at least substantially centered on the central axis. Each helical ridge may have a large pitch with the helical ridge extending more axially than circumferentially on the body portion. Driving the nail may drive the nail into a hole in the bone, with at least a portion of the band of connective tissue disposed in the hole. Driving may be performed by application of one or more pulses of axial force to the nail such that the helical ridges cause the nail to turn as the nail is advanced into the bone, to restrict removal of the nail from the hole and such that the portion of the band of connective tissue is secured in the hole between the bone and the nail in an interference fit.

The nail may include a body that includes (1) a shaft and (2) at least one helical ridge formed on the shaft and extending along and around any suitable portion of the shaft. The helical ridge may have a large pitch, that is, a pitch notably greater than the typical pitch of a bone screw, which is about three to five degrees. More specifically, a large pitch, as used herein, is provided by a helical ridge with an average lead angle of at least about fifty degrees. The large pitch permits the nail to be driven into bone or connective tissue like a pin, namely, by exerting at least substantially exclusively axial force on the nail (e.g., by pounding the nail into bone). The large pitch also may convert a portion of the axial driving force into a torque that gradually rotates the nail as it is driven into bone, without stripping a corresponding internal groove being formed in the bone by the helical ridge. The helical ridge thus may provide the nail with some of the advantages of a bone screw, such as reduced slippage, and better axial and rotational stability, by increasing contact and purchase with the bone and/or connective tissue. These advantages, in turn, may increase the effectiveness of the nail for fixation and/or repair.

Further aspects of the present disclosure are described in the following sections: (I) exemplary bone nail and method of use, (II) shaft, (III) helical ridges, (IV) composition of bone nails, (V) suitable bones and connective tissues, (VI) methods of installing bone nails, (VII) kits, and (VII) examples.

I. EXEMPLARY BONE NAIL AND METHOD OF USE

FIG. 1 shows a somewhat schematic exploded view of an exemplary embodiment of a bone nail 40 installed in a bone 42 and including one or more helical ridges of large pitch, which may be described as helical fins or ribs. In this example, bone 42 is a radial bone and nail 40 is disposed in a distal portion of the radial bone. However, any suitable bone and/or soft tissue may receive the bone nail. Nail 40 may be disposed in a spanning relation to a discontinuity 44, such as a fracture 46 and/or a cut, in the bone. In other words, the nail may extend across the discontinuity and into each of at least two bone pieces, which may or may not be discrete with respect to one another. For example, nail 40 may extend from a first bone fragment 48 to a discrete second bone fragment 50. The entire bone nail may be driven at least substantially completely into the bone or only partially into bone. If driven only partially into the bone, the nail may be shortened at any suitable time to separate an internal piece 52 from an external piece 54 of the bone nail.

Figure 2:
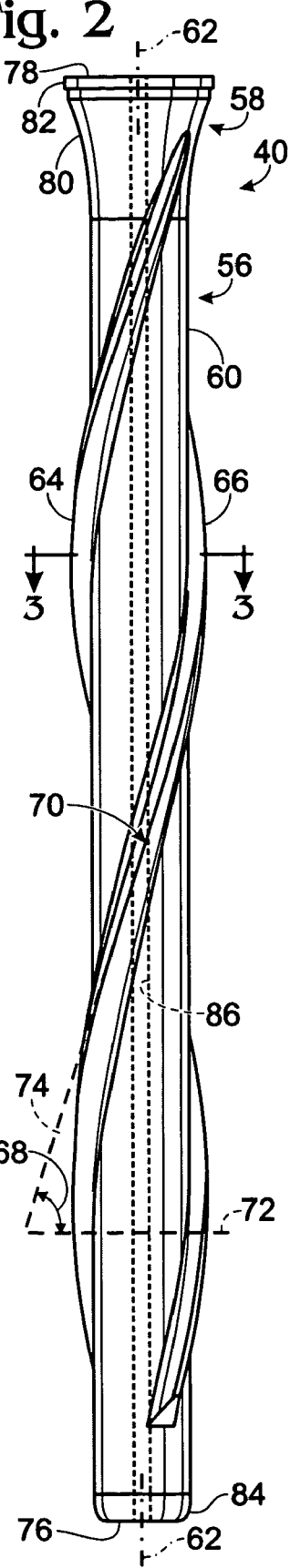
FIG. 2 is a side view of the bone nail of FIG. 1 in the absence of bone and before separation of the bone nail into two discrete pieces, in accordance with aspects of present disclosure.

FIG. 2 shows a side view of bone nail 40 of FIG. 1 in the absence of bone and before optional separation of the bone nail into discrete pieces. Bone nail 40 may include a body 56 and a head 58 arranged axially along the nail. The body and the head of the bone nail may be formed unitarily such that the bone nail is monolithic, which may be described as one-piece construction.

Body 56 may include a shaft 60 defining a central axis 62 and also may include at least one or two or more helical ridges 64, 66. The shaft may have a substantially circular cross section and thus may be substantially cylindrical, which means that the shaft has at least the general form of a single cylinder, with a diameter that is generally constant along the length of the cylinder or that decreases gradually along the length of the cylinder, to introduce a slight lengthwise taper of about five degrees or less. The helical ridges may be of about the same size and/or shape or may have distinct sizes and/or shapes. Each helical ridge may be formed on the shaft, with each helical ridge projecting at least generally radially from the shaft and at least substantially centered on the central axis. Each helical ridge may be formed on and/or may extend along any suitable portion of the length of the shaft and/or nail, such as along at least most or at least substantially all of the length of the shaft and/or nail. Furthermore, each helical ridge may be formed on at least most of the length of both a leading half and of a trailing half of the nail, which are arranged axially along the nail and form halves of the nail based on length.

A helical ridge, as used herein, generally comprises any ridge (i.e., a rib or fin) that extends in a generally spiral pattern both along and at least partially around the shaft. Each helical ridge may create a large pitch, which is any pitch provided by a helical ridge that extends more axially than circumferentially on the shaft, to form an average lead angle of greater than about fifty degrees. The term pitch, as used herein, corresponds to the slope (or lead angle) of a helical ridge, with a relatively larger pitch corresponding to a relatively larger slope (lead angle) and a smaller pitch corresponding to a relatively smaller slope (lead angle) of the helical ridge. A lead angle, as used herein, is the minimum angle defined between a tangent to a position on a helical ridge and a plane disposed orthogonally to the central axis, and is generally the complement of the helix angle, which is the angle formed by the tangent with respect to the central axis. In other words, the lead angle plus the helix angle for any position on a helical ridge equals ninety degrees. For the purposes of illustration, a ridge that extends only along, and not about, shaft 60, although not helical, would have a lead angle of ninety degrees and a ridge that extends only about, and not along, shaft 60, although not helical, would have a lead angle of zero degrees. The lead angle of the helical ridges discloses herein may, for example, be about sixty to eighty degrees, or about seventy-five degrees, among others.

An exemplary lead angle 68 defined by helical ridge 66 is shown in FIG. 2. Lead angle 68 is defined for a position 70 on helical ridge 66 between a plane 72 orthogonal to central axis 62 and a tangent 74 to position 70. The lead angle (and thus pitch) may be at least substantially constant along the helical ridge or may vary as shown here. If the lead angle (or pitch) varies, the lead angle (or pitch) may decrease gradually and/or smoothly towards the trailing end of the nail. A smooth decrease in lead angle (or pitch) is a decrease that avoids any sudden or stepwise changes in the lead angle. Furthermore, the lead angle (or pitch) may decrease towards the trailing end of the nail along at least most of the length of the helical ridge. In some embodiments, the pitch and/or lead angle may vary at least substantially uniformly along the length of the nail. In other words, the pitch and/or lead angle may exhibit an at least substantially constant rate of change per unit length of the nail.

Head 58 may extend from body 56 and shaft 60 of the nail. The head may promote contact with a driver by presenting a larger surface area to the driver and/or may improve compression of bone, relative to a comparable nail with no head, as the head is driven into bone.

The nail may have a leading end 76 and a trailing end 78 that define axial boundaries of the nail and thus a length of the nail. Body 56 and/or shaft 60 may form leading end 76 and head 58 may form trailing end 78. The body and/or shaft may extend along at least a major portion or all of the length of the nail, such as at least about three-fourths or seven-eights of the length, among others, and the head may extend along only a minor portion or none of the length of the nail (if the nail lacks a distinct head). The shaft may be slender, which means that the shaft has a length that is many times the average diameter of the shaft, namely, at least about five times or ten times the average diameter of the shaft.

Head 58 may be wider than body 56 and/or shaft 60, such as having a greater average diameter and/or maximum diameter than the shaft. Head 58 may taper toward (and flare away from) body 56 and shaft 60. For example, head 58 may have a flared region 80 that extends to a crown 82, which, in some embodiments, may be cylindrical or may taper opposingly with respect to flared region 80. Flared region 80 and thus at least a portion of head 58, may be at least generally frustoconical, as shown here.

Figure 3:
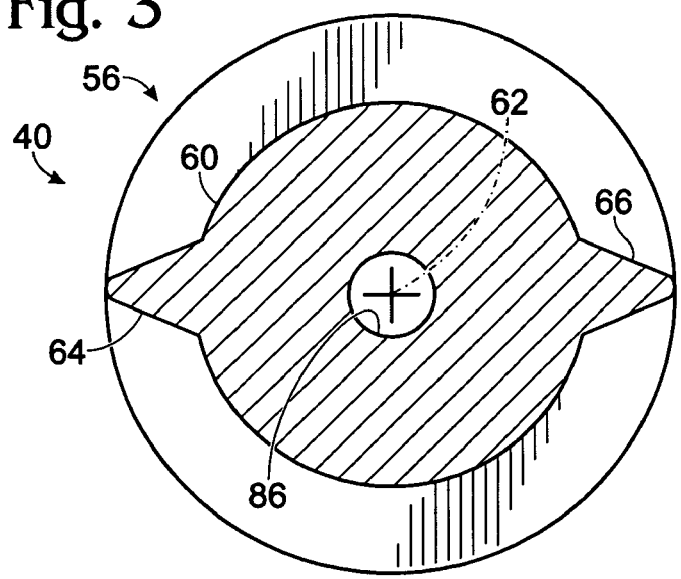
FIG. 3 is a cross-sectional view of the bone nail of FIG. 2, taken generally along line 3-3 of FIG. 2.

FIG. 3 shows a cross sectional view of nail 40. Helical ridges 64, 66 may be formed as fins/ribs, such as triangular fins/rib, which may project at least generally radially outward from shaft 60. The helical ridges may be displaced rotationally from one another, such as by one-half turn about central axis 62 to give the nail two-fold (180-degree) rotational symmetry.

Nail 40 may have any other suitable features. For example, shaft 60 may have an at least substantially uniform diameter along at least most of its length or may be tapered (e.g., see Example 2). In any event, a leading section of shaft 60 may taper as it approaches leading end 76 of the nail, to form a tapered tip 84 (see FIG. 2). The tip may promote entry into and travel along a hole in bone. Accordingly, head 58 and/or tapered tip 84 may provide a polarity to the bone nail. Furthermore, nail 40 may define a longitudinal passage 86 extending from leading end 76 to trailing end 78 such that the nail is cannulated. Passage 86, which may be described as an axial through-hole or bore, may be concentric with central axis 62.

FIGS. 4-8 shows a series of sectional views of fractured bone 42 in configurations produced during performance of an exemplary method of bone fixation using nail 40. However, more generally, the method may be performed using any suitable bone nail, including but not limited to any of the other bone nails shown and/or described in the present disclosure, including any suitable combination of the features thereof. The steps associated with the method may be performed in any suitable order, in any suitable combination, and any suitable number of times. In some embodiments, some of the steps may be omitted, and/or other steps may be added.

FIG. 4 shows a fragmentary, longitudinal sectional view of an exemplary bone to be fixed. The bone may, for example, be a radial bone that has sustained a fracture 46 distally to produce at least one bone fragment 48 that should be secured to a remainder and/or another bone fragment 50 of the bone. Although a radial bone is shown here, any suitable bone or bone-associated connective tissue may be repaired with a bone nail disclosed herein. If used to fix a bone, the bone nail may be installed in any suitable region of the bone, including a shaft (middle portion) and/or a head (end portion) of the bone. Here, the nail is being installed near the end of the radius bone where the bone cortex is relatively thin and cancellous bone predominates. In some examples, the nail may be installed primarily in cortical bone, cartilage, or ligament. Other applications include installation of the nail into a preformed (e.g., pre-drilled) hole and in engagement with a tendon or ligament as a soft tissue fixation technique (e.g., see Example 4).

A path for placement of the nail may be defined prior to installation of the nail. For example, a guide wire 90 may be driven, indicated at 92, into the bone, through bone fragment 48 and across fracture 46. In other examples, a pilot hole may be drilled into and/or through bone, or a guide device, such as a cannula, may be mounted on the bone. Alternatively, the nail may define its own path as it is being placed into bone.

FIG. 5 shows bone 42 after a hole 94 for receiving the bone nail has been formed in the bone. Accordingly, the method may include a step of drilling, over the guide wire (or without a guide wire), a hole for receiving the nail, using a cannulated drill. The hole may be a blind hole that extends into but not through the bone, as shown here, or the hole may be a through-hole that extends completely through the bone. The hole may have a diameter that corresponds to a crosswise dimension (e.g., the diameter) of the nail's shaft. For example, here, the shaft and the hole in bone have about the same diameter. The hole in bone may be slightly undersized crosswise, for better retention of the nail, or may be slightly oversized crosswise, for easier installation of the nail. For fixation of soft tissue (e.g., a tendon and/or ligament), the hole may be somewhat larger to account for the additional soft tissue to be fixated inside the hole by the nail (e.g., see Example 4).

FIG. 6 shows nail 40 being driven into hole 94 in the radial bone. A driver may be used to exert an at least predominantly axial force on the nail. Accordingly, the driver may be or include an impact or striking tool 96, such as a hammer or mallet, which may be used to strike the nail directly or may strike a force-transfer tool disposed over the nail (e.g., see Example 1). In any event, the driver may apply axial force to head 58 and/or trailing end 78 of the nail. The axial force may be in the form of one or more pulses. In some embodiments, axial force may be delivered by a driver or similar device configured to apply a relatively more continuous axial force of adjustable magnitude. In some embodiments, axial force may be applied to the nail with a practitioner's hand.

The axial force exerted by the driver may be converted to a torque by the action of the nail's helical ridge(s) bearing against bone. As a result, the nail may turn as it is being driven into bone, at a rate and extent determined by the pitch of the nail's ridge(s). For example, in the present illustration, nail 40 may rotate about one-half turn when driven to the depth of hole 94 (compare FIGS. 6 and 7) or about one full turn if it is driven at least substantially completely into the bone.

FIG. 7 shows nail 40 advanced to the bottom of pre-formed hole 94 in bone and thus driven a distance in bone corresponding to the depth of hole 94. A trailing portion 100 of the nail may protrude from the bone after the step of driving is complete. Alternatively, the nail may be advanced at least substantially fully into bone, such that trailing end 78 of the nail is substantially flush with a proximate, outer surface region of the bone (e.g., see Example 1). In any event, driving nail 40 into the bone may provide compression between pieces of the bone, such as to urge bone fragments 48 and 50 toward one another and to close a gap formed by discontinuity 46.

FIG. 8 shows separation of protruding, trailing portion 100 of the nail from a leading portion 102 of the nail that is disposed in bone (also see FIG. 7), to shorten the nail. In particular, the nail may be cut or broken near the bone surface to minimize protrusion of the nail above bone and to create internal piece 52 and discrete external piece 54 of the nail. Accordingly, the nail may be advanced to a selectable depth, to allow the same length of nail to be used more flexibly in bone fixation.

II. SHAFT

The shaft of the body may have any suitable size and shape. For example, the shaft may have a circular cross section to provide a substantially cylindrical shape having a generally uniform diameter or a diameter that decreases gradually along the length of the shaft. The substantially cylindrical shaft thus may be tapered slightly, such as tapering at an angle of about five degrees or less along at least most of its length to aid in bony compression. In some embodiments, a leading section of the shaft may be tapered or curved as it extends toward the leading end of the shaft, to form a tip that promotes entry into and travel along a hole in bone. The shaft (and/or helical ridges) thus may at least partially define a longitudinal asymmetry (a directionality) to the nail, such that the nail has a leading end and a trailing end that are not reversible. The shaft (and/or nail) may be elongated, with a length that is substantially greater than the average diameter of the shaft, such as at least about two, five, or ten times the average diameter.

The shaft may form any suitable portion of the exterior surface and volume of the nail's body. For example, in some embodiments, the helical ridges may be relatively narrow, and the shaft may form a majority of the exterior surface of the body (e.g., see Example 1). Furthermore, in some embodiments, the shaft and the helical ridges may collectively form the body with the shaft forming most of the body's volume. The use of relatively narrow ridges formed on only a minor portion (rather than on a major portion) of the shaft and/or ridges that collectively form only a minor portion (rather than forming a major portion) of the body's volume may reduce the axial force needed to drive the nail into bone, which may minimize damage to the bone.

The shaft may be solid or hollow. For example, in the latter case, the shaft may be cannulated to provide a central channel extending lengthwise through the nail. The channel may be used to fit the nail over a guide wire to facilitate placement of the nail.

The nail, as noted above, has a trailing end for receiving an axial force exerted on the nail by a driver. The trailing end may, for example, be flat (planar) to distribute the axial force uniformly across the nail. In some embodiments, the trailing end may be formed by a head disposed proximally of the shaft; the head may be any proximal widening of the nail. The head may serve to provide a larger target area for a driver, to restrict axial travel of the nail as the trailing end of the nail approaches or enters bone and, in turn, exert additional axial force on bone to provide some bony compression, and/or to secure a fixation device such as a bone plate disposed between the head and the bone, among others. The head may have any suitable shape. For example, the nail may flare as it extends from the shaft, to form a frustoconical head. The head also may have any suitable size. For example, the head may extend along the nail for substantially less than one-half the length of the nail, such as less than about twice the diameter of the head or less than about one-half the length of the trailing half of the nail, among others. In other cases, the nail may have no distinct head. In any event, the nail, in contrast to a bone screw, may be formed without engagement structure (i.e., without a slot, socket, flats (planar facets), hexagonal head, etc.) for a torque driver.

III. HELICAL RIDGES

The helical ridges of the shaft may have any suitable size, shape, and arrangement (e.g., pitch, number, etc.). For example, the helical ridges may be formed as fins that project generally radially outward from the shaft and that extend on an at least substantially spiral or helical path generally along and at least partway around the shaft. The helical ridges may facilitate stable placement of the nail, by increasing its contact and purchase with bone and/or connective tissue, making the nail more effective for fixation and repair.

The helical ridges may be continuous or interrupted in two or more segments. The segments may be spaced arbitrarily along and around the nail. The segments as well as the interruptions may be of equal or different lengths. The helical ridges may extend at least mostly and/or only partially over the length of the nail.

The helical ridges may have a pitch that is much greater than the pitch of an external thread on a bone screw. In particular, the helical ridges may extend at an average and/or minimum lead angle of greater than fifty degrees, and, in some embodiments, may extend at an average lead angle of sixty to eighty degrees, such that the helical ridges maximize the holding power in bone while not substantially increasing the insertion forces of the nail during implantation. The pitch may be constant or may vary (to make the pitch variable) as each helical ridge extends along the shaft. For example, the helical ridge may have a variable pitch with a decrease in pitch toward the trailing end of the nail, to provide compression of bone as the nail is installed. The helical ridge may have a lead angle that decreases by any suitable amount, such as decreasing by about one to five degrees per 10 mm of nail length, or by no more than about ten degrees per 10 mm of nail length, among others. In some exemplary embodiments, the lead angle may change by a total of about four to six degrees in a nail of about 20 to 40 mm total length.

The shape and/or dimension of the helical ridge may be consistent or may change over the nail length. For example, the helical ridge may be of triangular shape with an increase in the triangular angle formed by the crest of the ridge, as the ridge extends toward the trailing end of the nail, to provide increased contact area with bone towards the trailing end to increase compression during implantation. The height of the helical ridges may be constant or may vary along the shaft. For example, the height of the helical ridges may increase towards the trailing end of the nail to form a tapered ridge to aid in the bony compression.

A helical ridge may extend any suitable distance around the nail, depending on the pitch of the ridge, the diameter of the nail, and the length on the nail along which the ridge extends. For example, the helical ridge may extend less than one-half revolution, about one-half revolution, about one revolution, or more than one revolution, among others.

A helical ridge may be present alone in a nail (single-ridged nails) or in combination with other ridges (multi-ridged nails). Multi-ridged nails have at least two helical ridges (ridge 1, ridge 2, ..., ridge N), typically, but not necessarily, of about the same size and shape. The helical ridges on a multi-ridged nail may be displaced rotationally from one another, symmetrically or asymmetrically, about a central axis of the nail. The presence of two or more helical ridges, particularly when the helical ridges are arranged to give the nail rotational symmetry, may help to balance the nail and reduce eccentric forces. Exemplary multi-ridged arrangements include two helical ridges spaced about one-half turn from one another to give the nail two-fold (180-degree) rotational symmetry, three helical ridges spaced about one-third turn from one another to give the nail three-fold (120-degree) rotational symmetry, and N helical ridges spaced about one-Nth turn from one another to give the nail N-fold ([360/N]-degree) rotational symmetry.

IV. COMPOSITION OF BONE NAILS

The bone nail may be formed of any suitable biocompatible material(s) of sufficient strength to allow the nail to be driven by application of axial force. Exemplary biocompatible materials include (1) metals (for example, titanium or titanium alloys, alloys with cobalt and chromium (cobalt-chrome), stainless steel, etc.); (2) plastics (for example, ultra-high molecular weight polyethylene (UHMWPE), polymethylmethacrylate (PMMA), polytetrafluoroethylene (PTFE), polyetheretherketone (PEEK), nylon, polypropylene, and/or PMMA/polyhydroxyethylmethacrylate (PHEMA)); (3) ceramics (for example, alumina, beryllia, calcium phosphate, and/or zirconia, among others); (4) composites; (5) bioresorbable (bioabsorbable) materials or polymers (for example, polymers of $\alpha$-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-$\beta$-hydroxybutyrate, poly-$\beta$-hydroxypropionate, poly-$\delta$-valerolactone, other bioresorbable polyesters, and/or natural polymers (such as collagen or other polypeptides, polysaccharides (e.g., starch, cellulose, and/or chitosan), any copolymers thereof, etc.); (6) bone tissue (e.g., bone powder and/or bone fragments); and/or the like. In some embodiments, these materials may form the core of the bone nail and/or a coating thereon. The materials may be non-resorbable or partially or completely resorbable, as desired or appropriate.

V. SUITABLE BONES AND CONNECTIVE TISSUES

The bone nails of the present disclosure generally may be used for the fixation and/or repair of any suitable bone and/or connective tissue.

The bone (or bone member) may, for example, be an intact bone(s) or may be one or more fragments of a bone produced by breaking or cutting the bone, among others. Exemplary bones for receiving a bone nail may include one or more bones of the hand/wrist (carpals, metacarpals, and/or phalanges), arms (radius, ulna, and/or humerus), legs (femur, tibia, fibula, and/or patella), feet (metatarsals, phalanges, calcaneus), shoulders (glenoid, acromion, coracoid, clavicle, scapula), ribs, vertebrae, pelvic bones, cranial bones, and/or the mandible, among others. In some examples, two or more bone members may be selected for receiving a bone nail. The two or more bone members may correspond to different bones or distinct fragments of the same bone, among others. The bone members may be adjacent one another naturally or may be moved so that they are adjacent one another. The bone members may have sustained or be associated with any suitable injury. For example, the bone members may result from an injury to bone (such as a fracture and/or an osteotomy, among others) or may be adjacent and/or connected to injured soft/connective tissue (e.g., ligament, tendon, and/or muscle, among others). In some examples, the bone members may be bones that articulate with one another through a suitable anatomical joint.

The connective tissue may, for example, be orthopedic connective tissue, namely, tendon, ligament, meniscus, and/or muscle, and may be a band of connective tissue. The band of connective tissue selected may have a size (e.g., width, diameter, and/or thickness) such that a section of the band can be disposed in a hole in a bone and/or can receive the bone nail. Accordingly, in some cases, the methods may involve creating a connection between a band of connective tissue and a bone member using a bone nail.

VI. METHODS OF INSTALLING BONE NAILS

The bone nails of the present teachings may be installed in bone and/or connective tissue by any suitable methods. These methods may include selecting a bone and/or connective tissue for repair, selecting a bone nail (or nails) for use in effecting the repair, placing a guide wire to facilitate formation of the hole and/or guidance of the bone nail, forming a hole in the bone and/or connective tissue to receive the bone nail, driving the bone nail into the bone, and/or removing portions of the bone nail that protrude from the bone, among others (see, e.g., Section I and Examples 1 and 4). The bone nail(s) selected may have any suitable combination of the features described in the present teachings. For example, the bone nail(s) may or may not have a head, a tip, and/or a variable pitch ridge, among others. The bone nail(s) may have a size (e.g., length and width) selected according to the size of the bone member(s) (and/or connective tissue) into which the bone nail is to be placed (e.g., a narrower and/or shorter bone nail for smaller bone members, a wider and/or longer bone nail for larger bone members, and a stockier nail for a shallow hole across a long bone). The steps involved in installing the bone nail may be performed in any suitable order, in any suitable combination, any suitable number of times, and optionally in connection with additional steps (including, optionally, in connection with other methods and devices for fixing bone and/or connective tissue, such as bone screws, bone plates, and wires, among others).

Bone nails may be left in place indefinitely/permanently after installation or may be removed at a later time. If left in place, a portion (e.g., a coating) or all of the bone nail may be bioresorbable such that the portion or all of the bone nail is broken down and absorbed by the body over time. If removed, removal of the bone nail may take place at any suitable time. Exemplary times include at a predefined or suitable time after installation or after a predefined or suitable amount of healing, among others.

VII. KITS

The bone nails of the present teachings may be provided as systems or in kits. A system or kit optionally may include any suitable combination of (1) one or more bone nails of the same and/or different sizes, (2) one or more drills and/or other tools for forming cavities (holes) in bone for receiving the bone nails, (3) one or more drivers and/or other tools (such as pounding tools (also termed impact tools), force-transfer tools (e.g., punch tools), gripping tools, clamping tools, and/or cutting tools (e.g., a wire cutter)) for installing and/or removing the bone nails, (4) one or more guide members such as guide wires for extending into/through bone and guiding the bone nails, drills, and/or drivers, as appropriate, (5) a cannula to protect the soft tissue and provide external guidance to nails, drills, and/or drivers, and/or (6) a case for holding and/or organizing other components of the system or kit. Components of the system or kit may be sterile and/or sterilizable (e.g., autoclavable). In some examples, components of the system or kit, such as the bone nails and/or guide wires, may be intended or suitable for single use. In some examples, components of the system or kit, such as cannulas, drivers, and/or drills may be intended or suitable for repeated use.

VII. EXAMPLES

The following examples describe selected aspects and embodiments of the present disclosure. These examples are included for illustration and are not intended to define or limit the entire scope of the present disclosure. The features and aspects in these examples may be combined, as desired or appropriate, with features and aspects described in other examples and/or elsewhere in the present disclosure.

Example 1

Exemplary Method of Nail Installation

Figure 9:
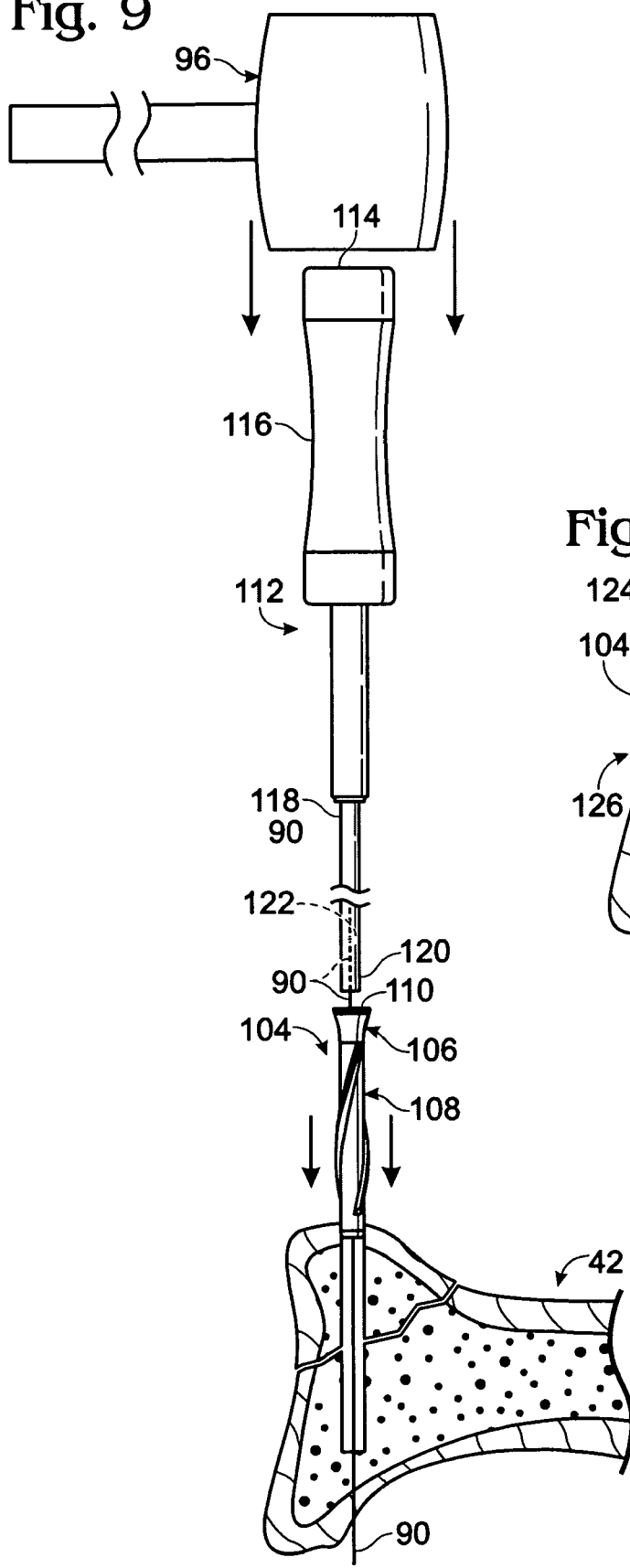
FIGS. 9 and 10 are a pair of sectional views of the fractured bone of FIG. 1 in configurations produced during performance of another exemplary method of bone fixation using a second exemplary embodiment of a nail, which is shorter than the nail of FIGS. 1-3, in accordance with aspects of the present disclosure.
Figure 10:
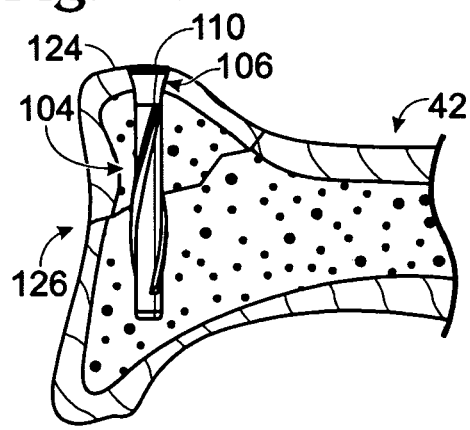

This example describes another exemplary method of nail installation; see FIGS. 9 and 10. Any suitable aspects of the method described in this example may be combined with aspects of the method described elsewhere herein, such as above in Sections I and VI.

FIG. 9 shows a configuration of fractured bone 42 produced as an exemplary bone nail 104 is being driven into the bone. Bone nail 104 may be shorter than bone nail 40 (see Section I) and may include any of the features disclosed elsewhere in the present disclosure, such as a tapered head 106 connected to a body 108. The bone nail also has a trailing boundary that forms a trailing end 110.

The bone nail may be struck directly with an impact tool 96 or axial force may be transferred from the impact tool to the nail via a force-transfer tool 112, such as a punch tool, which may be described as a plunger. The force-transfer tool may be disposed in contact with the nail when struck with impact tool 96, but is shown spaced from the nail in the present illustration to improve clarity. The force-transfer tool may form a target surface 114 for the impact tool over the nail. The target surface may be more spaced from bone than trailing end 110 of the nail, to reduce the chance of accidentally striking the bone with the impact tool. Also, the target surface of the force-transfer tool may have a greater area and/or diameter than the trailing end of the nail.

Force-transfer tool 112 may include a head 116 connected to a stem 118. Head 116 may provide target surface 114. Stem 118 may form a tip 120 that contacts a trailing end region, such as head 106, of the nail. Tip 120 may bear against trailing end 110 of bone nail 104 or may be received in the nail, among others. In any event, tip 120 may have a diameter that is about the same as or less than the diameter of the bone nail, near or at the trailing end thereof, to avoid damaging bone when the tip of the force-transfer tool applies an axial force to the bone nail near the surface of the bone. Furthermore, tip 120 may define an axial passage 122 sized to receive an end portion of guide wire 90, which may permit the guide wire to restrict lateral motion of tip 120 to a position off of or at least out of alignment with the bone nail. Axial passage 122, which may be described as an axial bore, may extend any suitable portion or all of the length of the force-transfer tool.

FIG. 10 shows fractured bone 42 fixed by nail 104 after the nail, including at least a portion of tapered head 106, has been driven into bone. The nail may be driven at least substantially fully into the bone such that trailing end 110 of the nail is at least substantially flush with respect to a proximate, outer surface region 124 of bone 42. Driving at least a portion of a head of the bone nail into bone may provide compression of the bone, as indicated at 126 in FIG. 10. Testing shows that compression of a bone with the bone nails disclosed herein may be increased by driving at least a portion of a tapered head into bone. Although not wishing to be bound by any theory of operation, increased compression may be caused by elastic deformation of bone and/or the bone nail as the head of the nail is driven into bone.

Example 2

Exemplary Bone Nail with Varying Pitch

Figure 11:
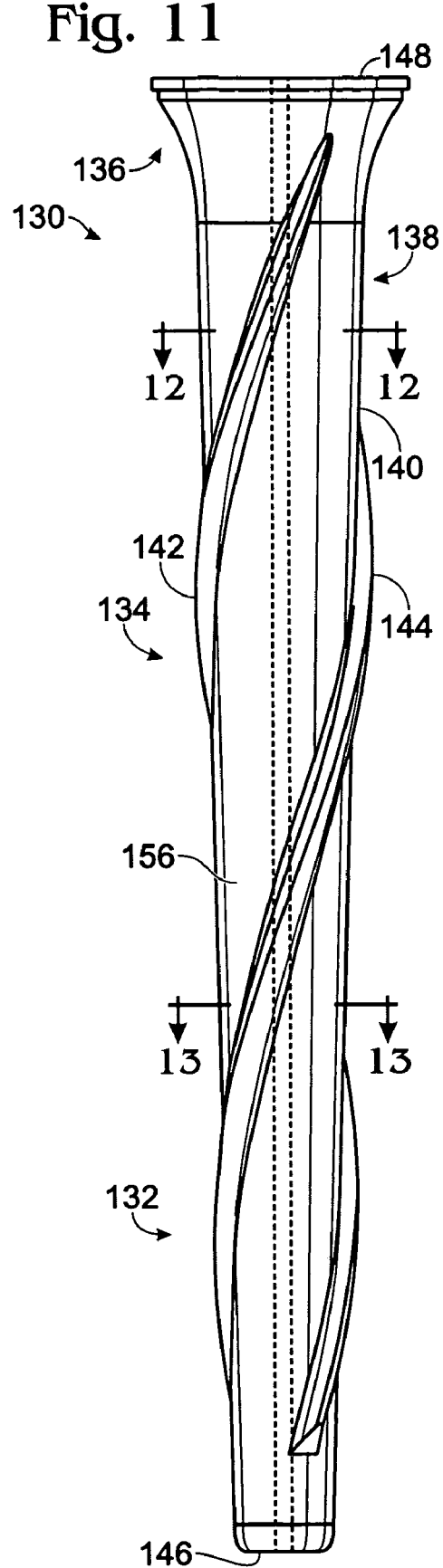
FIG. 11 is a side view of a third exemplary embodiment of a bone nail constructed in accordance with aspects of present disclosure, with the bone nail including a tapered shaft and helical ridges that taper in height and width.
Figure 12:
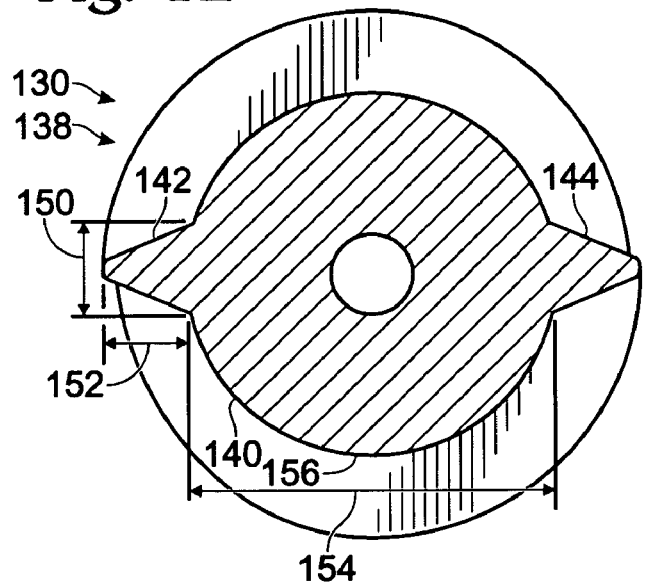
FIG. 12 is a cross-sectional view of the bone nail of FIG. 11, taken generally along line 12-12 of FIG. 11.
Figure 13:
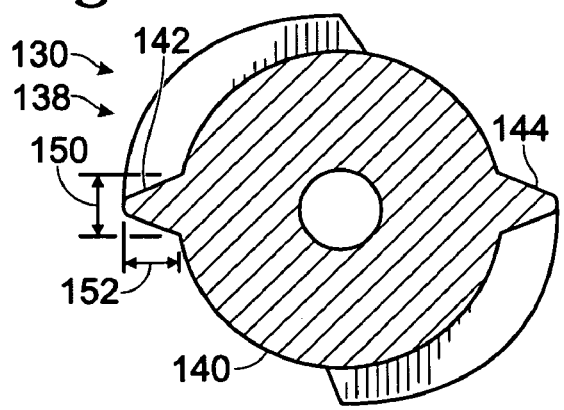
FIG. 13 is another cross-sectional view of the bone nail of FIG. 11, taken generally along line 13-13 of FIG. 11.

This example describes an exemplary tapered bone nail 130 with helical ridges of varying pitch; see FIGS. 11-13.

FIG. 11 shows a side view of bone nail 130. The bone nail may be divided conceptually into a leading portion 132 and a trailing portion 134 arranged axially along the bone nail. The bone nail may include a head 136 extending from a body 138. The body may include a shaft 140 and at least one or two or more helical ridges 142, 144 formed on the shaft. Each helical ridge may have any of the properties of helical ridges described in the present disclosure. Furthermore, each helical ridge may have a varying pitch. In particular, each ridge may have a relative increase in pitch toward a leading end 146 of the nail, and a relative decrease in pitch toward a trailing end 148 of the nail. Accordingly, a pitch of each helical ridge in leading portion 132 may be greater than the pitch of such helical ridge in trailing portion 134 with a gradual decrease in pitch toward the trailing end, thereby providing compression between pieces of a bone when the nail is driven into the bone.

FIGS. 12 and 13 show cross-sectional views of bone nail 130 taken, respectively, at relatively more trailing and leading positions along the nail. Shaft 140 may vary in diameter along its length (compare FIGS. 12 and 13). For example, shaft 140 may taper toward leading end 146 along at least most or least substantially all of the shaft's length (also see FIG. 11). The use of a tapered shaft may improve compression of bone. A suitable amount of taper for the shaft may be a slight taper, which may be about five degrees or less, among others.

Helical ridges 142, 144 may vary in width along their length. In particular, each helical ridge has a width 150 measured at a base of such helical ridge adjacent the shaft (see FIGS. 12 and 13). The width of at least one helical ridge may increase as the at least one helical ridge extends generally toward trailing end 148 of the bone nail, such that the at least one helical ridge tapers in width toward leading end 146 of the nail (compare width 150 in FIGS. 12 and 13). The use of helical ridges that taper in width may improve compression of bone, and/or may fasten the nail more securely to bone by forming an increasingly wider groove in bone as the nail is advanced into bone.

The helical ridges may vary in height along their length. In particular, each helical ridge has a height 152 measured radially from the shaft (see FIGS. 12 and 13). The height of at least one helical ridge may increase as the at least one helical ridge extends generally toward trailing end 148 of the bone nail, such that the at least one helical ridge tapers in height 152 toward leading end 146 of the nail (compare height 152 in FIGS. 12 and 13). The use of helical ridges that taper in height may improve compression of bone, and/or may fasten the nail more securely to bone by forming an increasingly deeper groove in bone as the nail is advanced into bone.

The helical ridges may occupy any suitable portion of the circumference of the shaft. In some examples, the helical ridges may be formed on only a minority of the circumference of the shaft. In particular, width 150 of at least one helical ridge, at the base of such helical ridge near the shaft, may be less than a width 154 of a helical surface 156 of the shaft formed between an adjacent pair of the helical ridges (see FIGS. 11 and 12). In other words, the width of the at least one helical ridge may be less than the spacing between adjacent helical ridges. In some embodiments, the shaft may form a major portion of the body's exterior surface, and the external ridges may form only a minor portion of the body's exterior surface.

Example 3

Exemplary Bone Nails-Selected Embodiments

This example describes various exemplary embodiments of axially driven bone nails having a large pitch; see FIGS. 14-19.

FIG. 14 shows a bone nail 160 including helical ridges 162, 164 of large pitch and discontinuous structure. Each helical ridge may be divided into two or more spaced ridge segments 166 that extend along the same helical path. The ridge segments (and the ridges in other embodiments) may be disposed such that each of their opposing ends is spaced from both ends of the nail.

FIG. 15 shows a bone nail 180 that may be installed without pre-forming a hole in bone. Nail 180 may have any of the features described in the present disclosure including helical ridges of large pitch. However, nail 180 may be more slender, solid instead of cannulated, and more pointed to provide a pointed tip 182 for forming a path in target tissue. In some cases, nail 180 may be suitable for use in tissue that is softer than bone, such as for repair of cartilage or ligament and/or to re-attach soft tissue to bone. In exemplary embodiments, nail 180 may be suitable for repair of the meniscus of the knee.

FIG. 16 shows a bone nail 200 including helical ridges of large pitch and a head 202 that projects orthogonally. Head 202 may be at least generally cylindrical.

FIG. 17 shows a bone nail 220 having a stepped head 222. The stepped head may be formed of a plurality of distinct head segments 224 of different diameter.

Figure 18:
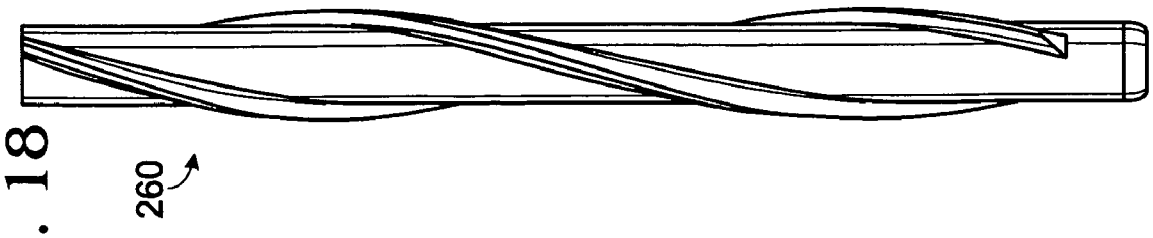
FIG. 18 is a side view of an eighth exemplary embodiment of a bone nail constructed in accordance with aspects of the present disclosure, with the bone nail lacking a head.

FIG. 18 shows a bone nail 260 constructed in accordance with aspects of the present disclosure, with the bone nail lacking a distinct head.

Figure 19:
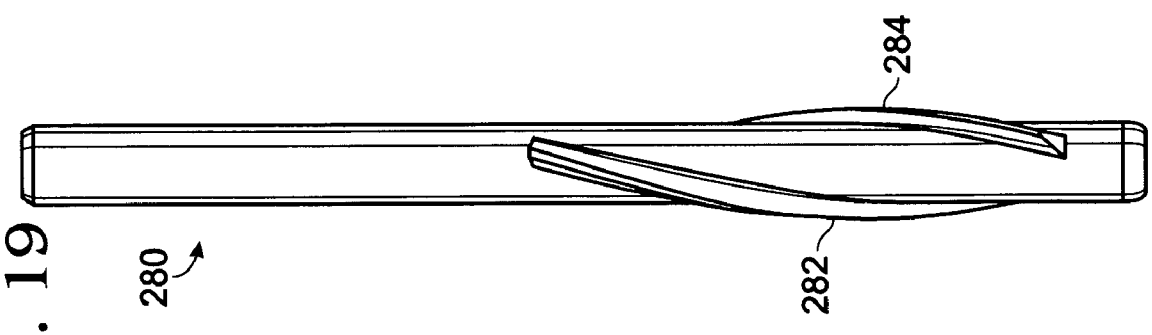
FIG. 19 is a side view of a ninth exemplary embodiment of a bone nail constructed in accordance with aspects of the present disclosure, with the bone nail including helical ridges that extend along only about one-half the length of the nail.

FIG. 19 shows a bone nail 280 including helical ridges 282, 284 that extend along only about one-half the length of the nail.

Example 4

Exemplary Bone Nail for Soft Tissue Attachment

This example describes a bone nail 300 formed as a plug and a method of using the bone nail to attach soft tissue to bone; see FIGS. 20-23.

Figure 20:
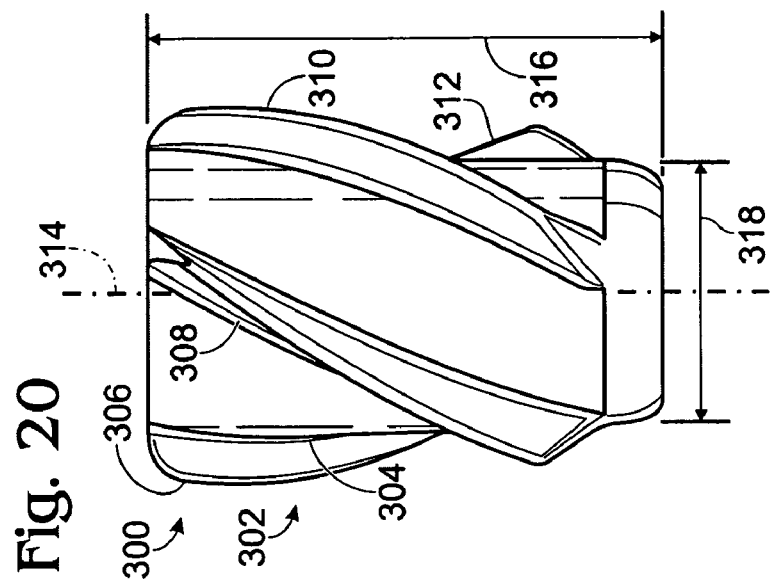
FIG. 20 is a side view of a tenth exemplary embodiment of a bone nail constructed in accordance with aspects of present disclosure, with the bone nail configured as a plug for attaching soft tissue to bone.

FIG. 20 shows a side view of bone nail 300. Bone nail 300 may have any combination of the features described elsewhere in the present teachings. The bone nail may include a body 302 that provides a body portion 304 and also may include at least one helical ridge, such as a plurality of helical ridges 306-312 (e.g., two or more) formed on the body portion. Body portion 304 may have any of the features described in the present disclosure for a nail's shaft. For example, body portion 304 may have a circular cross section, may be substantially cylindrical, and/or may define a central through-hole for receiving a guide wire.

Bone nail 300 may differ in being relatively short and stout. Nail 300 and/or body portion 304 may define a central axis 314, may have a characteristic dimension 316 (e.g., a length) measured parallel to the central axis, and may have a diameter 318 measured perpendicular to the central axis. The characteristic dimension of the body portion may be less than and/or about the same as the diameter of the body portion, may be less than about three times the diameter, or may be about one to three times the diameter, among others. Bone nail 300 may be particularly suited to be an interference implant for tendon and/or ligament fixation.

Figure 21:
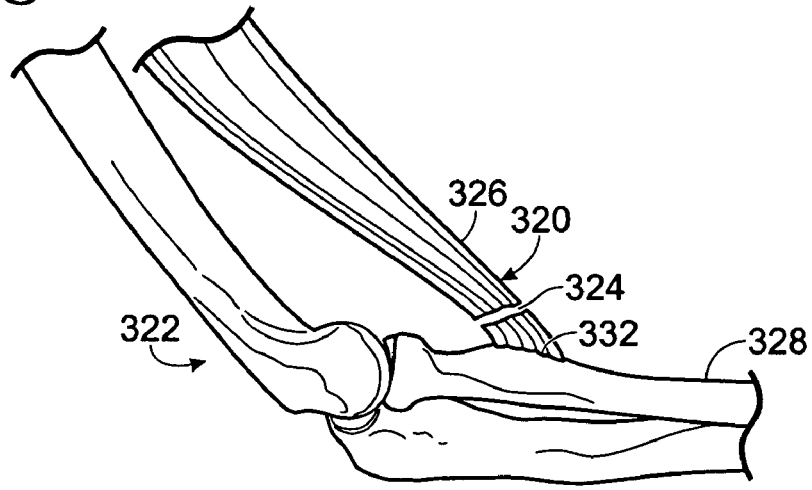
FIGS. 21-23 are a series of fragmentary views of a biceps tendon and associated bones in configurations produced during performance of an exemplary method of attaching soft tissue to bone using the nail of FIG. 20, in accordance with aspects of the present disclosure.
Figure 22:
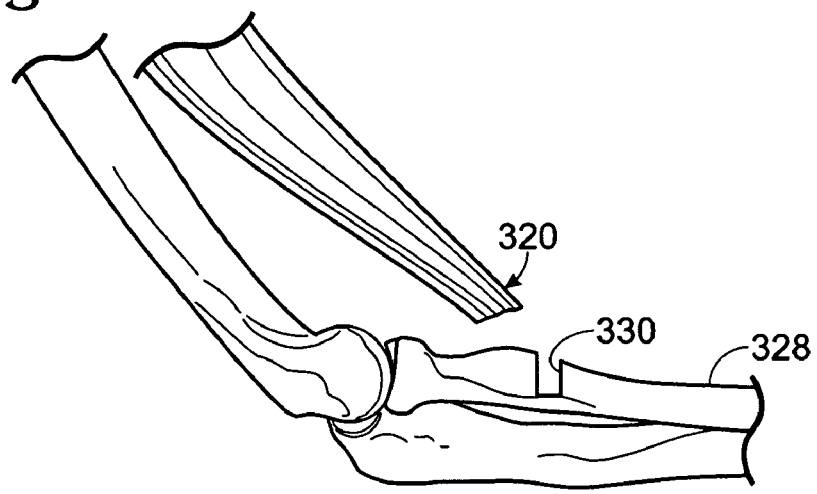
Figure 23:
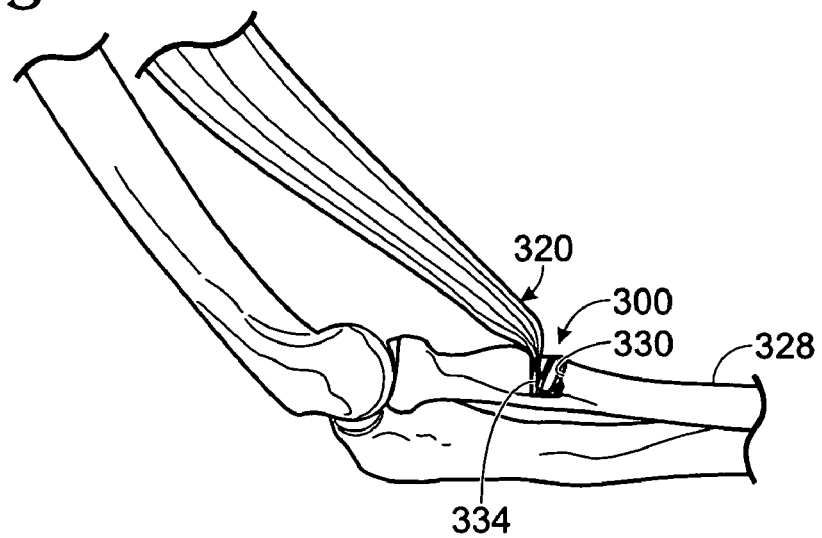

FIGS. 21-23 show a series of fragmentary views of a biceps tendon 320 and an elbow region 322 of a skeleton in configurations produced during performance of an exemplary method of attaching soft tissue to bone using nail 300 (see FIG. 20). In other examples, any other suitable soft tissue and/or bone may be used in the method.

FIG. 21 shows biceps tendon 320, which may be described as a band of soft tissue, in an injured condition that includes a tear 324 in the tendon. Alternatively or in addition, biceps tendon 320 may be cut surgically or otherwise damaged in structural integrity. In any event, a portion 326 of biceps tendon 320 may be detached from a radial bone 328 of elbow region 322.

FIG. 22 shows a hole 330 pre-formed in radial bone 328, generally positioned according to an anatomical attachment-site 332 for the biceps tendon on the radial bone (see FIG. 21). Hole 330 may be sized in correspondence with a crosswise dimension of body portion 304 of bone nail 300 (see FIG. 20). For example, hole 330 may have a diameter that is slightly more than the diameter of body portion 304, to permit both the biceps tendon and nail 300 to be received in the radial bone.

FIG. 23 shows bone nail 300 disposed in hole of radial bone 328, after driving the bone nail into bone by application of at least predominantly axial force to the bone nail. A portion 334 of biceps tendon 320 may be secured in the hole between bone nail 300 and the bone, to fix the portion of the biceps tendon to the bone.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

The invention claimed is:

1. A method of fastener installation in bone, comprising:
   selecting a nail including a substantially cylindrical shaft and two or more helical ridges formed on the shaft along at least most of the length of the nail, each helical ridge having an average lead angle of about 60 to 80 degrees and a variable pitch that decreases toward a trailing end of the nail;
   driving at least part of the nail into bone by application of axial force to the nail such that the helical ridges cause the nail to turn and form grooves in the bone complementary to the helical ridges as the nail is advanced into the bone, thereby securing the nail in the bone;
   wherein the step of driving causes the nail to span a discontinuity in the bone; and
   wherein the step of driving includes a step of striking the nail or a tool disposed adjacent the nail.

2. The method of claim 1, wherein the length of the shaft is at least about five times the average diameter of the shaft.

3. The method of claim 1, wherein the shaft and the helical ridges collectively form a body of the nail, and wherein the shaft forms most of the body's volume.

4. The method of claim 1, wherein the nail flares near the trailing end to form a head.

5. The method of claim 1, wherein the average width of at least one helical ridge is less than an average width of a helical surface of the shaft formed between an adjacent pair of the helical ridges.

6. The method of claim 1, wherein each helical ridge projects at least generally radially from the shaft to an average height that is less than an average radius of the shaft.

7. The method of claim 1, wherein at least one of the helical ridges is discontinuous between opposing ends of the at least one helical ridge.

8. The method of claim 1, wherein each helical ridge has a height measured radially from the shaft, and wherein the height of at least one helical ridge increases as the at least one helical ridge extends generally toward the trailing end.

9. The method of claim 1, wherein each helical ridge has a width measured at a base of such helical ridge adjacent the shaft, and wherein the width of at least one helical ridge increases as the at least one helical ridge extends generally toward a trailing end of the nail.

10. The method of claim 1, wherein the shaft tapers towards a leading end of the nail along at least most of the shaft's length.

11. The method of claim 1, further comprising a step of forming a hole in the bone before the step of driving, wherein the hole has a crosswise dimension corresponding to a diameter of the shaft, and wherein the step of driving disposes at least a portion of the shaft in the hole.

12. The method of claim 1, wherein the step of driving includes a step of advancing the nail along a guide wire disposed in the bone.

13. The method of claim 1, wherein the step of driving disposes the nail in contact with the bone along at least substantially all of the length of the nail.

14. The method of claim 1, wherein the nail has a trailing surface that faces at least generally opposite to a direction in which the nail is driven into the bone, and wherein the step of driving disposes the trailing surface at least substantially flush or recessed with respect to a proximate, outer surface region of the bone.

15. The method of claim 1, further comprising a step of shortening the nail after the step of driving.

16. A method of fastener installation in bone, comprising:

selecting a nail including a substantially cylindrical shaft and two or more helical ridges formed on the shaft along at least most of the length of the nail, each helical ridge having an average lead angle of about 60 to 80 degrees and a variable pitch that decreases toward a trailing end of the nail;

driving at least part of the nail into bone by application of axial force to the nail such that the helical ridges cause the nail to turn and form grooves in the bone complementary to the helical ridges as the nail is advanced into the bone, thereby securing the nail in the bone;

wherein the step of driving causes the nail to span a discontinuity in the bone;

wherein the shaft and the helical ridges collectively form a body of the nail;

wherein the shaft forms most of the body's volume; and wherein the step of driving includes a step of striking the nail or a tool disposed adjacent the nail.

17. The method of claim 16, wherein each helical ridge projects at least generally radially from the shaft to an average height that is less than an average radius of the shaft.

18. The method of claim 16, wherein the nail has a trailing surface that faces at least generally opposite to a direction in which the nail is driven into the bone, and wherein the step of driving disposes the trailing surface at least substantially flush or recessed with respect to a proximate, outer surface region of the bone.

* * * * *